(12) United States Patent
Huang

(10) Patent No.: US 9,060,834 B2
(45) Date of Patent: Jun. 23, 2015

(54) METHOD FOR POSITIONING ORTHODONTIC BRACES

(71) Applicant: EZBOND CO., LTD., New Taipei (TW)

(72) Inventor: Cheng-Ho Huang, New Taipei (TW)

(73) Assignee: EZBOND CO., LTD., New Taipei (TW)

( * ) Notice: Subject to any disclaimer, the term of this patent is extended or adjusted under 35 U.S.C. 154(b) by 24 days.

(21) Appl. No.: 14/267,411

(22) Filed: May 1, 2014

(65) Prior Publication Data

US 2014/0329195 A1   Nov. 6, 2014

(30) Foreign Application Priority Data

May 2, 2013   (TW) .............................. 103113526 A

(51) Int. Cl.
*A61C 3/00* (2006.01)
*A61C 11/08* (2006.01)
*A61C 7/00* (2006.01)

(52) U.S. Cl.
CPC ................. *A61C 11/08* (2013.01); *A61C 7/002* (2013.01)

(58) Field of Classification Search
CPC ........... A61C 11/08; A61C 7/002; A61C 7/00
USPC ................................................. 433/8–12, 24
See application file for complete search history.

(56) References Cited

U.S. PATENT DOCUMENTS

| | | | | |
|---|---|---|---|---|
| 4,200,980 | A * | 5/1980 | Johnston | 433/8 |
| 8,235,717 | B2 * | 8/2012 | Kuperman | 433/24 |
| 2007/0031775 | A1 * | 2/2007 | Andreiko | 433/24 |
| 2010/0190125 | A1 * | 7/2010 | Lee | 433/3 |

* cited by examiner

*Primary Examiner* — Yogesh Patel
(74) *Attorney, Agent, or Firm* — Muncy, Geissler, Olds & Lowe, P.C.

(57) ABSTRACT

A method for positioning orthodontic braces includes scanning a patient's teeth by a computer in which installation locations of orthodontic braces for the teeth to be cured are arranged; carving out by a carving machine a denture mold and positioning members at the installation locations of the orthodontic braces on the denture mold to attach monomer substrata bound with the orthodontic braces or the orthodontic braces connected serially by connection members onto the denture mold one by one; connecting the monomer substrata together by light curing resin; attaching the serially connected monomer substrata and orthodontic braces directly onto the patient's teeth, and removing flexible members binding the monomer substrata and monomer substrata or the connection members connecting the orthodontic braces serially to secure the orthodontic braces on the surfaces of teeth, which installs the orthodontic braces more conveniently and efficiently.

4 Claims, 9 Drawing Sheets

METHOD FOR POSITIONING ORTHODONTIC BRACES

BACKGROUND OF THE INVENTION a) Field of the Invention

The present invention relates to a method for positioning orthodontic braces, and more particularly to a method which sets up positioning members at locations of the orthodontic braces on a patient's denture mold, such that the orthodontic braces can be latched and located to the positioning members, thereby enabling the orthodontic braces to be installed more conveniently and efficiently.

b) Description of the Prior Art

Normally in curing malocclusion, the surfaces of teeth are attached with orthodontic braces and then all the orthodontic braces are connected tightly. A conventional way to installing the orthodontic braces is described generally below:
1. A denture mold is made according to a patient's teeth condition.
2. Cross lines are drawn on the denture mold and wax is coated on an inner rim of the denture mold.
3. The orthodontic braces are aligned to the inner rim of the denture mold based upon the cross lines, and then a single unit of monomer substratum is produced with powder forming.
4. The substrata are bound with the orthodontic braces using flexible members.
5. Upon installing, the orthodontic braces are coated with an adhesive material and then attached onto the patient's teeth one by one.
6. The flexible members and the monomer substrata are removed, such that the orthodontic braces can be secured on the surfaces of teeth. Next, all the orthodontic braces are connected, which accomplishes installing the orthodontic braces.

The abovementioned conventional method for manufacturing and installing the orthodontic braces can be only used in accordance with a patient's teeth condition and the substrata should be made by a professional denture mold technician. In addition, as the orthodontic braces should be located accurately in advance, the entire process of manufacturing and installation will spend a lot of time and labor, which is not efficient. Furthermore, the installation cost will be higher, and this increases a patient's economic pressure. Accordingly, a method for positioning orthodontic braces is disclosed, such that the orthodontic braces can be installed more conveniently.

SUMMARY OF THE INVENTION

The primary object of present invention is to provide a method for positioning orthodontic braces, wherein locations of the orthodontic braces are set up on a patient's denture mold, and positioning members are provided at the locations of these orthodontic braces to latch and locate the orthodontic braces, thereby enabling the orthodontic braces to be installed more conveniently and efficiently.

In the abovementioned method for positioning the orthodontic braces, a patient's teeth are first scanned by a computer, and then the installation locations of the orthodontic braces for the teeth to be cured are arranged in the computer to facilitate carving out a denture mold by a carving machine. In a mean time, the positioning members are carved out at the installation locations of the orthodontic braces on the denture mold, such that the monomer substrata that are bound with the orthodontic braces or the orthodontic braces that are connected serially by connection members can be attached onto the denture mold one by one to latch and locate the orthodontic braces to the positioning members. Next, all the monomer substrata are connected together by light curing resin, such that upon installing the orthodontic braces, the serially connected monomer substrata and orthodontic braces can be attached directly onto the patient's teeth. Afterward, the flexible members binding the orthodontic braces and the monomer substrata or the connection members connecting the orthodontic braces serially are removed, such that the orthodontic braces can be secured on the surfaces of teeth, thereby enabling the orthodontic braces to be installed more conveniently and efficiently.

In the abovementioned method for positioning the orthodontic braces, the positioning member is a frame unit having a wall portion of proper height.

To enable a further understanding of the said objectives and the technological methods of the invention herein, the brief description of the drawings below is followed by the detailed description of the preferred embodiments.

DETAILED DESCRIPTION OF THE PREFERRED EMBODIMENTS

Figure 1:
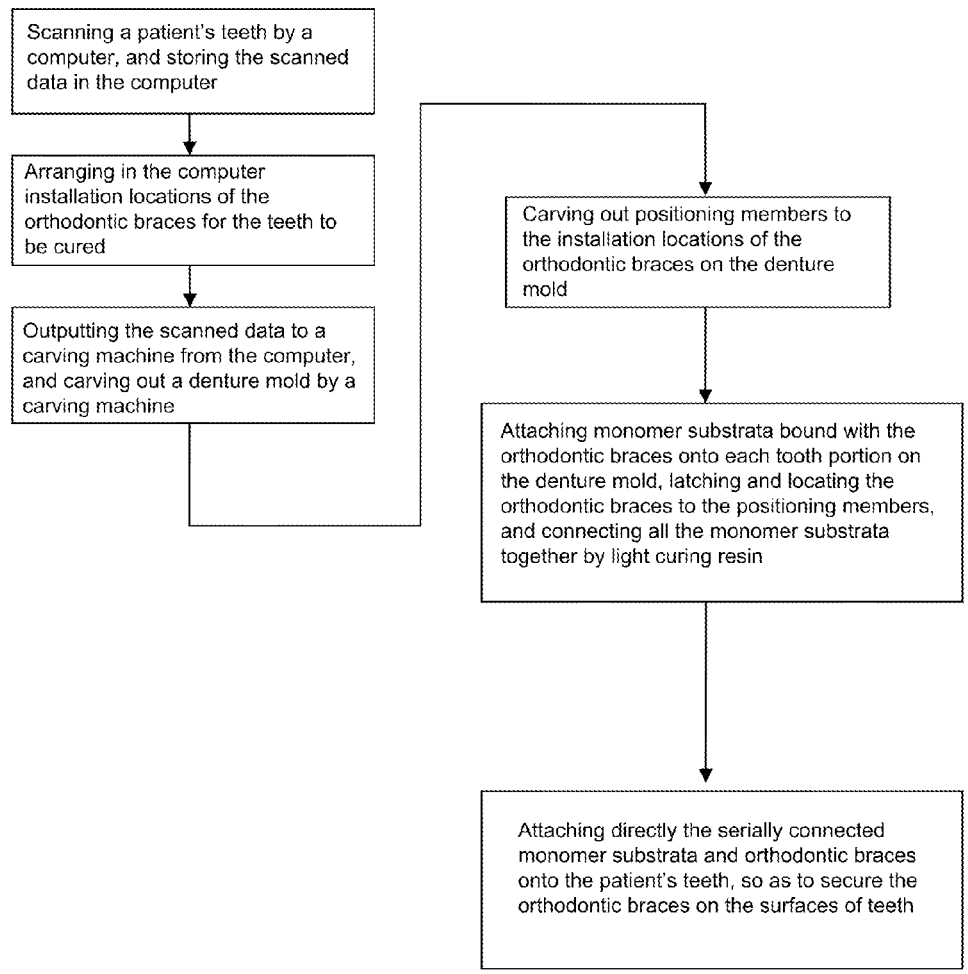
FIG. 1 shows a flow diagram of a manufacturing process of the present invention.

Referring to FIG. 1, it shows a flow diagram of a manufacturing process, according to the present invention. As shown in the drawing, the manufacturing process of the present invention comprises following steps:
1. A patient's teeth are scanned by a computer as a basis for making a denture mold. The scanned data are stored in the computer.
2. Installation locations of the orthodontic braces for the teeth to be cured are arranged in the computer (display screen).
3. Locations of the positioning members to be provided are set up on the denture mold for each tooth portion at a lips side (exterior side).
4. The scanned data are outputted to a carving machine from the computer and the denture mold is carved out by the carving machine. In a mean time, the positioning members are carved out at the installation locations of the orthodontic braces on the denture mold.

5. The monomer substrata that are bound with the orthodontic braces are attached onto each tooth portion on the denture mold, such that the orthodontic braces can be latched and located to the positioning members. Next, all the monomer substrata are connected together by light curing resin.

6. When installing the orthodontic braces, the serially connected monomer substrata and orthodontic braces are attached directly onto the patient's teeth, and then the flexible members binding the orthodontic braces and the monomer substrata are removed, such that the orthodontic braces can be secured on the surfaces of teeth, thereby enabling the orthodontic braces to be installed more conveniently and efficiently.

Figure 2:
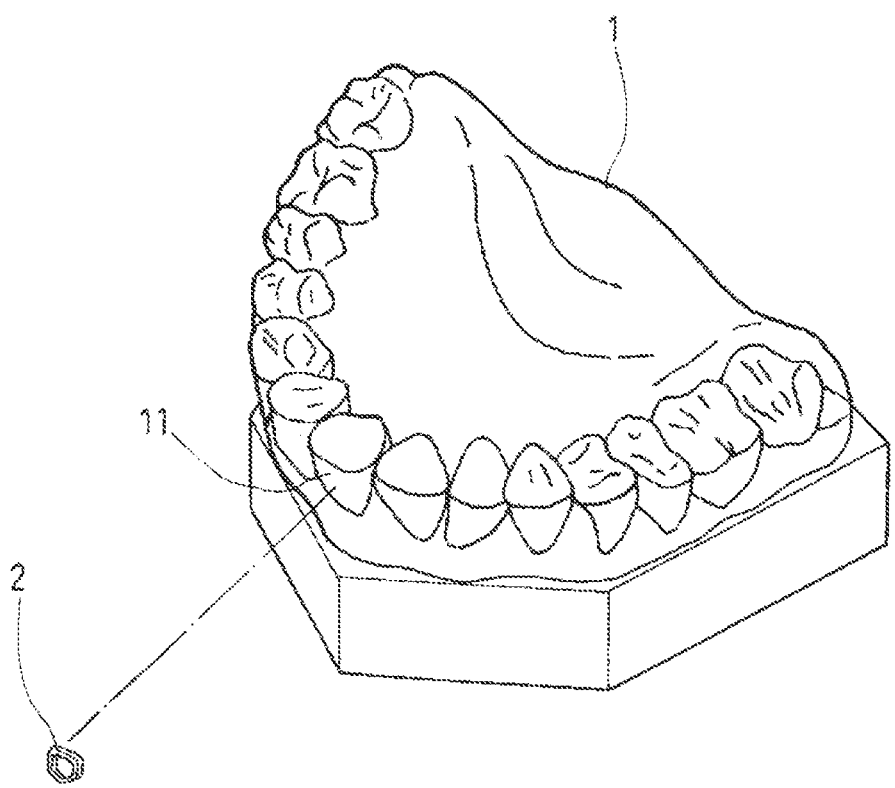
FIG. 2 shows a schematic view of a first embodiment of manufacturing at a lips side, according to the present invention.
Figure 3:
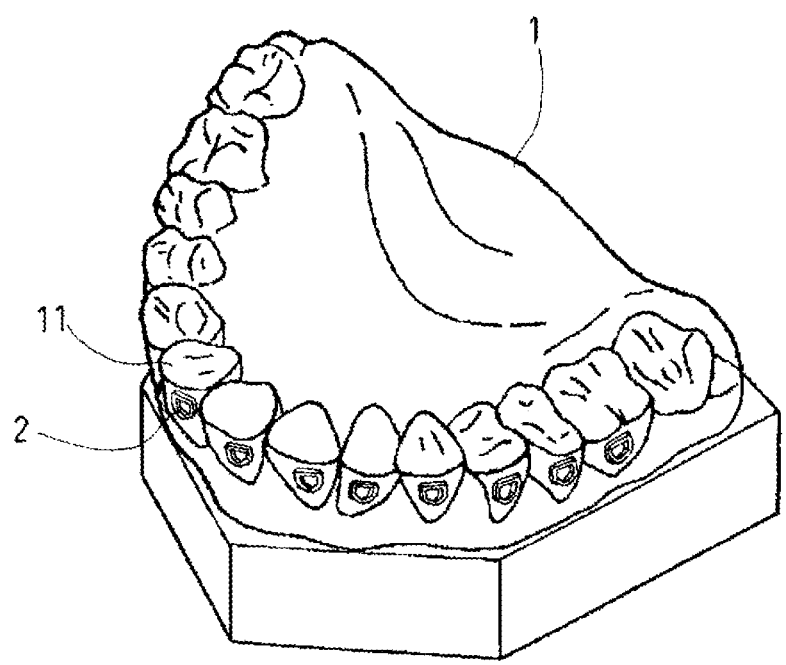
FIG. 3 shows another schematic view of the first embodiment of manufacturing at the lips side, according to the present invention.

Referring to FIG. 2 and FIG. 3 at a same time, it shows schematic views of a first embodiment of manufacturing at a lips side, according to the present invention. As shown in the drawings, a patient's teeth are scanned by a computer, and the scanned data are stored in the computer. Next, installation locations of the orthodontic braces for the teeth to be cured are arranged in the computer (display screen), and each tooth portion on the denture mold 1 is set up with a recess portion for carving. The scanned data are outputted to a carving machine from the computer and the denture mold 1 is carved by the carving machine. In a same time, the positioning members 2 are carved out at the tooth portions 11 on the denture mold 1. In the present embodiment, the positioning member 2 is a frame unit having a wall portion of proper height.

Figure 4:
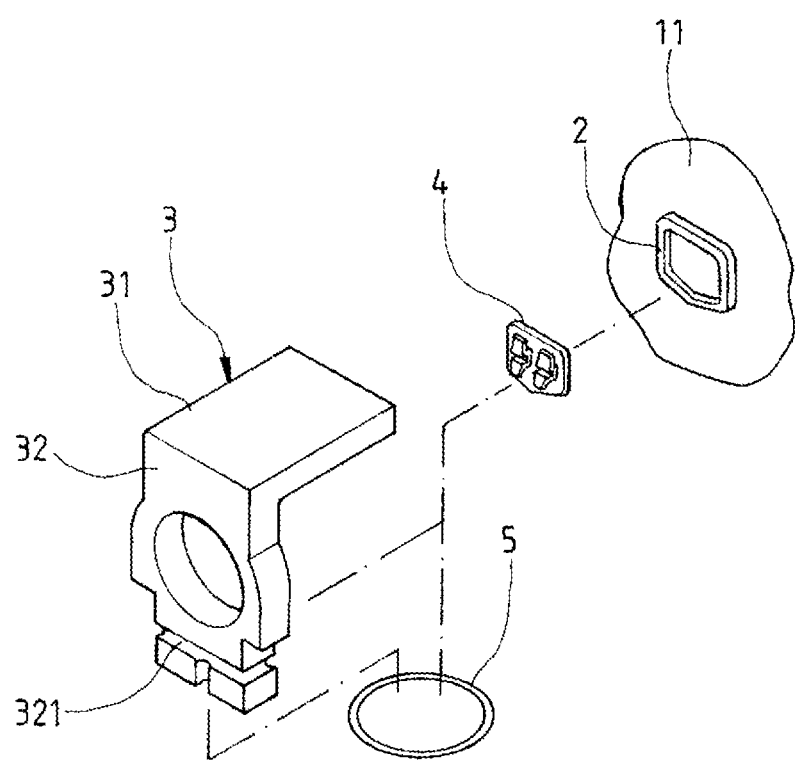
FIG. 4 shows a schematic view of an embodiment of securing orthodontic braces at the lips side, according to the present invention.
Figure 5:
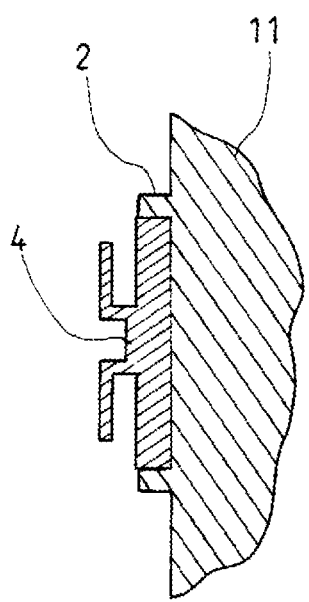
FIG. 5 shows a cutaway view of securing the orthodontic braces at the lips side, according to the present invention.

Referring to FIG. 4 and FIG. 5 at a same time, it shows a schematic view and a cutaway view of an embodiment of securing the orthodontic braces at the lips side, according to the present invention. As shown in the drawings, after accomplishing the denture mold 1 as described above, a monomer substratum 3 which is made by plastic injection molding (the monomer substratum 3 includes a horizontal hook portion 31 and a vertical portion 32 extending downward from the horizontal hook portion 31, the vertical portion 32 is provided with a transversal positioning groove 321 at a proper location, and the orthodontic brace 4 is bound along the positioning groove 321 by a flexible member 5, such that the orthodontic brace 4 can be latched at a rear edge of the vertical portion 32 of the monomer substratum 3) is used to bind the orthodontic brace 4, and then all the abovementioned monomer substrata 3, along with the orthodontic braces 4 that are bound with the monomer substrata 3, are attached onto the denture mold 1, enabling all the orthodontic braces 4 to be latched and located to the positioning members 2 that are set up for the tooth portions 11 on the denture mold 1.

Figure 6:
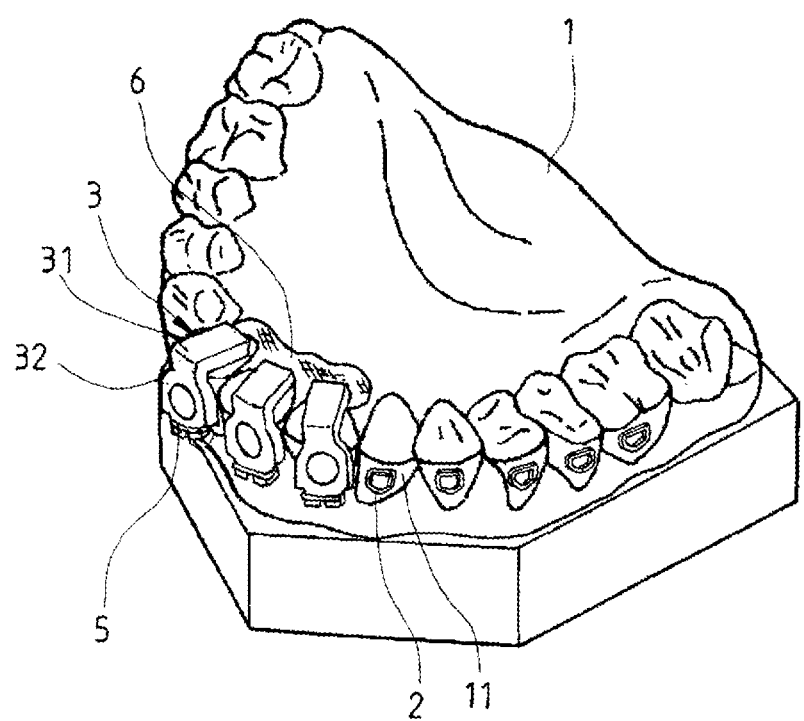
FIG. 6 shows a schematic view of a second embodiment of manufacturing at the lips side, according to the present invention.

Referring to FIGS. 4 and 6, it shows a schematic view of a second embodiment of manufacturing at the lips side, according to the present invention. As shown in the drawing, after each monomer substratum 3, along with the orthodontic brace 4 that is bound with the monomer substratum 3, is attached onto the denture mold 1, and each orthodontic brace 4 is latched and located to the positioning member 2 of each tooth portion 11 on the denture mold 1, light curing resin 6 is attached onto each abovementioned monomer substratum 3, allowing all the monomer substrata 3 to be connected together by the light curing resin 6. Afterward, the serially connected monomer substrata 3 and orthodontic braces 4 that are bound with the monomer substrata 3 are taken down from the denture mold 1. Next, each orthodontic brace 4 is gummed, and the serially connected monomer substrata 3, along with the orthodontic braces 4 that are bound with the monomer substrata 3, are attached directly onto the tooth portions to be cured. When the gum is set, the flexible members 5 that bind the monomer substrata 3 are removed by a specific tool and the monomer substrata 3 are dismantled from the orthodontic braces 4, such that the orthodontic braces 4 can be secured on the surfaces of teeth to be cured. Therefore, a dentist can connect tightly the orthodontic braces 4 to accomplish installing the orthodontic braces 4.

Figure 7:
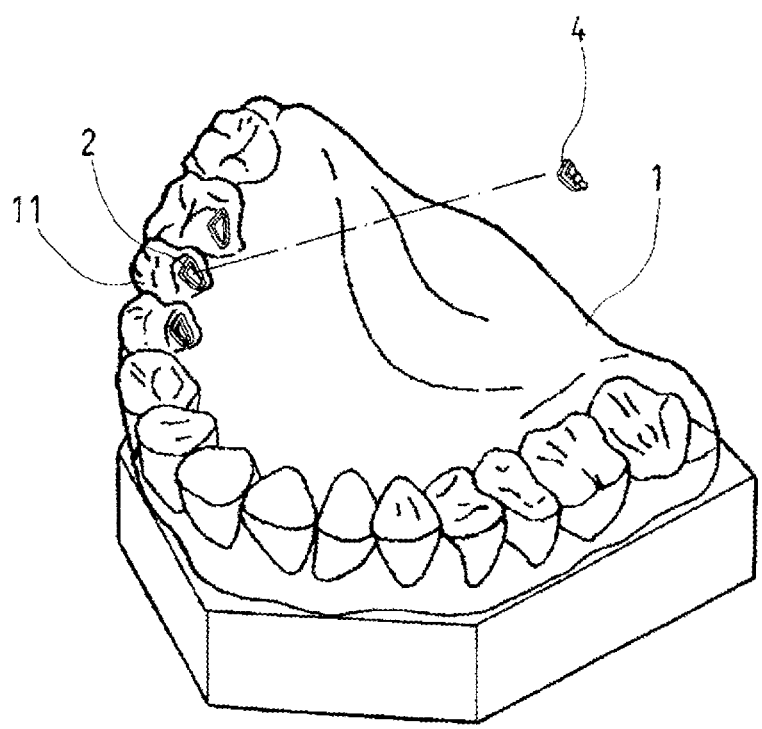
FIG. 7 shows a schematic view of an embodiment of manufacturing at a tongue side, according to the present invention.
Figure 8:
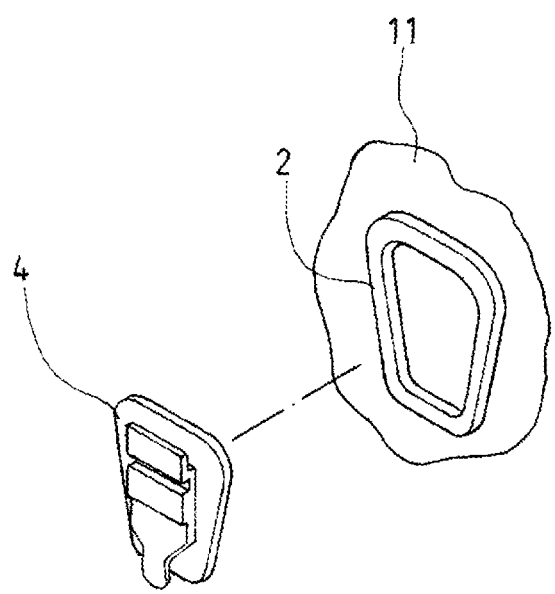
FIG. 8 shows another schematic view of the embodiment of manufacturing at the tongue side, according to the present invention.

Referring to FIG. 7 and FIG. 8 at a same time, it shows schematic views of an embodiment of manufacturing at a tongue side (inner side), according to the present invention. As shown in the drawings, when the present invention is to be implemented on the tongue side, the same way as that is implemented on the lips side is performed; that is, the installation locations of the orthodontic braces 4 for the teeth to be cured are arranged in the computer, and the positioning members 2 are carved out at the installation locations of the orthodontic braces 4 on the denture mold 1, such that the orthodontic braces 4 can be latched and located to the positioning members 2.

Figure 9:
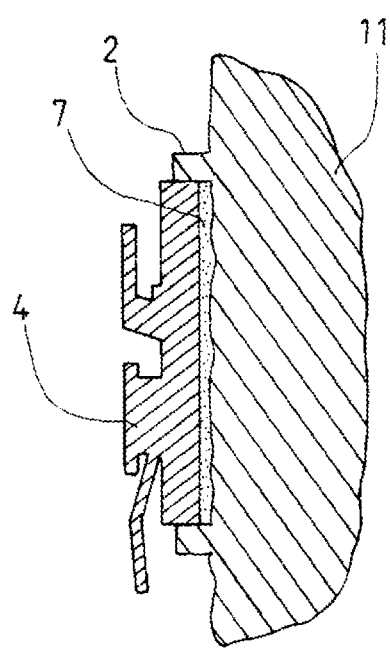
FIG. 9 shows a cutaway view of securing the orthodontic braces at the tongue side, according to the present invention.

Referring to FIG. 9, it shows a cutaway view of securing the orthodontic braces at the tongue side, according to the present invention. As shown in the drawing, for the orthodontic braces 4 of the present invention to be secured at the tongue side, as the tooth portions 11 at the tongue side are not very tidy, therefore, upon latching the orthodontic brace 4 to the positioning member 2, a certain gap should be preserved between the orthodontic brace 4 and the tooth portion 11 and an adhesive material 7 is filled into this gap, which prevents the orthodontic brace 4 from being offset.

Accordingly, the present invention discloses a method for positioning the orthodontic braces, wherein by the denture mold that are provided the positioning members, along with the monomer substrata that are bound with the orthodontic braces, the orthodontic braces can be latched and located to the positioning members, thereby enabling the orthodontic braces to be installed more conveniently and efficiently.

It is of course to be understood that the embodiments described herein is merely illustrative of the principles of the invention and that a wide variety of modifications thereto may be effected by persons skilled in the art without departing from the spirit and scope of the invention as set forth in the following claims.

What is claimed is:

1. A method for positioning orthodontic braces, comprising steps of:
 a) carving a denture mold according to a patient's teeth condition and arranging installation locations of the orthodontic braces for the teeth to be cured on the denture mold;
 b) carving out positioning members at the installation locations of the orthodontic braces on the denture mold;
 c) attaching monomer substrate which are bound with the orthodontic braces onto each tooth portion on the denture mold, latching and locating the orthodontic braces to the positioning members, and connecting the monomer substrate together by light curing resin; and
 d) upon installing the orthodontic braces, attaching the serially connected monomer substrate and orthodontic braces onto the patient's teeth directly, and removing flexible members that bind the orthodontic braces and the monomer substrate, allowing the orthodontic braces to be secured on the surfaces of teeth.

2. The method for positioning the orthodontic braces according to claim 1, wherein the positioning member is a frame unit having a wall portion of proper height.

3. The method for positioning the orthodontic braces according to claim 1, wherein the denture mold is manufactured by scanning a patient's teeth with a computer, storing the scanned data in the computer, and arranging in the computer installation locations of the orthodontic braces for the teeth to be cured.

4. The method for positioning the orthodontic braces according to claim 1, wherein the denture mold is manufactured by outputting a patient's scanned data to a carving machine from a computer, and carving out the denture mold by the carving machine.

* * * * *